United States Patent
Sebillotte-Arnaud et al.

(10) Patent No.: US 9,526,682 B2
(45) Date of Patent: *Dec. 27, 2016

(54) FINE O/W EMULSION

(75) Inventors: Laurence Sebillotte-Arnaud, L'Hay les Roses (FR); Odile Aubrun, Paris (FR)

(73) Assignee: L'OREAL, Paris (FR)

( * ) Notice: Subject to any disclaimer, the term of this patent is extended or adjusted under 35 U.S.C. 154(b) by 1290 days.

This patent is subject to a terminal disclaimer.

(21) Appl. No.: 11/154,687

(22) Filed: Jun. 17, 2005

(65) Prior Publication Data

US 2006/0013783 A1    Jan. 19, 2006

Related U.S. Application Data

(60) Provisional application No. 60/590,924, filed on Jul. 26, 2004.

(30) Foreign Application Priority Data

Jul. 16, 2004 (FR) .................................... 04 51547

(51) Int. Cl.
| | | |
|---|---|---|
| *A61K 8/06* | (2006.01) | |
| *A61K 8/34* | (2006.01) | |
| *A61K 8/39* | (2006.01) | |
| *A61K 8/31* | (2006.01) | |
| *A61K 8/37* | (2006.01) | |
| *A61K 8/02* | (2006.01) | |
| *A61Q 1/04* | (2006.01) | |
| *A61Q 1/14* | (2006.01) | |
| *A61Q 5/00* | (2006.01) | |
| *A61Q 5/12* | (2006.01) | |
| *A61Q 9/02* | (2006.01) | |
| *A61Q 17/04* | (2006.01) | |
| *A61Q 19/00* | (2006.01) | |
| *A61Q 19/10* | (2006.01) | |

(52) U.S. Cl.
CPC ............... *A61K 8/37* (2013.01); *A61K 8/0212* (2013.01); *A61K 8/062* (2013.01); *A61K 8/31* (2013.01); *A61Q 1/04* (2013.01); *A61Q 1/14* (2013.01); *A61Q 5/00* (2013.01); *A61Q 5/12* (2013.01); *A61Q 9/02* (2013.01); *A61Q 17/04* (2013.01); *A61Q 19/00* (2013.01); *A61Q 19/10* (2013.01); *A61K 2800/28* (2013.01)

(58) Field of Classification Search
CPC ........... A61K 8/062; A61K 8/068; A61K 8/37
USPC .......................................... 424/401
See application file for complete search history.

(56) References Cited

U.S. PATENT DOCUMENTS

| | | |
|---|---|---|
| 4,606,913 A | 8/1986 | Aronson et al. |
| 5,498,406 A | 3/1996 | Nearn et al. |
| 6,013,271 A * | 1/2000 | Doughty et al. ............. 424/401 |
| 6,086,787 A | 7/2000 | Schambil et al. |
| 6,221,370 B1 | 4/2001 | Wadle et al. |
| 6,537,562 B1 | 3/2003 | Boettcher et al. |
| 6,623,746 B1 | 9/2003 | Wadle et al. |
| 2003/0181602 A1 * | 9/2003 | Ansmann et al. ............ 525/418 |

FOREIGN PATENT DOCUMENTS

| | | |
|---|---|---|
| DE | 195 32 543 | 3/1997 |
| EP | 0 667 144 | 8/1995 |
| EP | 1 120 101 | 8/2001 |
| EP | 1 120 102 | 8/2001 |
| EP | 2 809 010 | 11/2001 |
| JP | 05070320 | 3/1993 |
| JP | 11279021 | 10/1999 |
| JP | 11343212 | 12/1999 |
| WO | WO 02/064107 | 8/2002 |

OTHER PUBLICATIONS

U.S. Appl. No. 11/154,602, filed Jun. 17, 2005, Sebillotte-Arnaud, et al.

* cited by examiner

*Primary Examiner* — Gina Justice

(74) *Attorney, Agent, or Firm* — Oblon, McClelland, Maier & Neustadt, L.L.P.

(57) ABSTRACT

The present invention relates to a composition containing lipophilic phase (A), an emulsifying system (B), and an aqueous phase (C) that is preferably suitable for topical use, in particular cosmetic and/or dermatological use, in the form of a fine oil-in-water emulsion that is rich in oil and can be obtained by phase inversion, and to uses thereof in particular in the cosmetics or dermatological field.

14 Claims, No Drawings

FINE O/W EMULSION

REFERENCE TO PRIOR APPLICATIONS

This application claims priority to U.S. provisional application 60/590,924 filed Jul. 26, 2004, and to French patent application 0451547 filed Jul. 16, 2004, both incorporated herein by reference.

FIELD OF THE INVENTION

The present invention relates to a composition preferably suitable for topical use, in particular cosmetic and/or dermatological use, in the form of a fine oil-in-water emulsion that is rich in oil and can be obtained by phase inversion, and to uses thereof in particular in the cosmetics or dermatological field.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

It is known practice, in the cosmetics or dermatological field, to use oil-in-water (O/W) emulsions. These emulsions, that have an oil phase (or lipophilic phase) dispersed in an aqueous phase, have an external aqueous phase and are therefore products that are more pleasant to use because of the feeling of freshness that they provide. However, they have the drawback of relatively lacking stability when the amount of oil present is too great. Now, for some applications, it is advantageous to have a large amount of oils since the oils provide comfort for the skin, nourish it, and can also remove makeup from it when these oils have makeup-removing properties.

Moreover, it is advantageous to have fine emulsions, i.e. emulsions where the oily phase is in the form of very small droplets, i.e. of droplets less than 4 µm in size, since these fine emulsions have a pleasant cosmetic feel and are generally more stable than coarse emulsions.

These emulsions can be prepared in particular by the phase inversion temperature technique (PIT emulsions), in which the average size of the globules constituting the oily phase is within given limits, namely between 0.1 and 4 µm (100 to 4000 nm). The principle of phase inversion temperature (or PIT) emulsification is, in theoretical terms, well known to those skilled in the art; it was described in 1968 by K. Shinoda (J. Chem. Soc. Jpn., 1968, 89, 435). It was shown that this emulsification technique makes it possible to obtain stable fine emulsions (K. Shinoda and H. Saito, J. Colloid Interface Sci., 1969, 30, 258). This technology was applied in cosmetics as early as 1972 by Mitsui et al. ("Application of the phase-inversion-temperature method to the emulsification of cosmetics"; T. Mitsui, Y. Machida and F. Harusawa, American. Cosmet. Perfum., 1972, 87,33).

The principle of this technique is as follows: an O/W emulsion (introduction of the aqueous phase into the oily phase) is prepared at a temperature that should be greater than the phase inversion temperature of the system, i.e. the temperature at which the equilibrium between the hydrophilic and lipophilic properties of the emulsifier(s) used is attained; at higher temperature, i.e. greater than the phase inversion temperature (>PIT), the emulsion is of water-in-oil type and, as it cools, this emulsion inverts at the phase inversion temperature so as to become an emulsion of oil-in-water type, having beforehand passed through a state of microemulsion. This process makes it possible to readily obtain emulsions with a diameter generally less than 4 µm. Emulsifying surfactants of the oil-in-water type conventionally used have an HLB (HLB=hydrophilic lipophilic balance) ranging from 8 to 18. These emulsifiers, due to their amphiphilic structure, are situated at the oil phase/aqueous phase interface, and thus stabilize the dispersed oil droplets.

However, it is difficult to produce fine O/W emulsions containing a large amount of oily phase, since such emulsions have a tendency to destabilize, this destabilization resulting in coalescence and separation of the aqueous and oily phases with release of the oil. In order to improve the stability of these emulsions, the concentration of emulsifiers can be increased; however, a high concentration of emulsifiers can result in a rough, clingy or sticky feel, and in problems of innocuity with respect to the skin, the eyes and the scalp.

Document WO-A-01/89678 describes oil-rich emulsions containing 70% of oil, this oil being dicaprylyl ether. However, the stability of these emulsions is not sufficient, as shown in the comparative examples presented below, in particular comparative example 1.

There therefore remains a need for providing fine O/W emulsions containing a large amount of oils while at the same time being stable.

SUMMARY OF THE INVENTION

The inventors have found, surprisingly, that the choice of certain oils in specific amounts makes it possible to obtain stable fine emulsions that also have good cosmetic properties.

DETAILED DESCRIPTION OF THE PREFERRED EMBODIMENTS

One subject of the present invention is therefore a composition in the form of an oil-in-water emulsion, comprising:
  a lipophilic phase (A) present in an amount of at least 50% by weight relative to the total weight of the composition, the lipophilic phase comprising at least 25% by weight of one or more synthetic or mineral hydrocarbon-based oils having a molecular weight greater than or equal to 360 g/mol,.relative to the total weight of the lipophilic phase,
  an aqueous phase (C) present in an amount of less than or equal to 45% by weight relative to the total weight of the composition,
  an emulsifying system (B) present in an amount of 2 to 20% by weight relative to the total weight of the composition and comprising at least one emulsifier having an HLB ranging from 8 to 18, chosen from ethoxylated fatty alcohols, ethoxylated fatty acids, partial glycerides of ethoxylated fatty acids, polyglycerolated fatty acid triglycerides and ethoxylated derivatives thereof and mixtures thereof,
  the emulsifying system (B)/lipophilic phase (A) ratio ranging from 0.04 to 0.2.

Because the invention composition is preferably intended for topical application, the composition of the invention preferably contains a physiologically acceptable medium. The term "physiologically acceptable medium" is intended to mean a medium suitable for topical application to the skin or the integuments, i.e. compatible with the skin, the mucous membranes, the lips, the eyelashes, the eyes, the hair and the nails. This composition can in particular constitute a cosmetic or dermatological composition.

In the present application, the term "lipophilic phase" is intended to mean the phase containing the lipophilic compounds, namely, in particular oils (lipophilic constituents that are liquid at ambient temperature), gums, pastes and waxes. They are, for example, triglycerides, hydrocarbons, esters, ethers, silicones, as described below, and any of the lipophilic additives optionally present. The emulsifiers and co-emulsifiers of the emulsifying system are not part of the lipophilic phase as defined above.

It is important to have a sufficient amount of lipophilic phase and in particular of oils in order to obtain a creamy texture, and a problem that forms part of the basis of the invention was the difficulty in obtaining a composition having a creamy texture with small-sized globules, that contains sufficient oils while at the same time nevertheless being very stable.

According to a preferred embodiment of the invention, the composition also preferably comprises at least one polyol as described in greater detail below.

The O/W emulsions according to the invention are preferably obtained by means of phase inversion temperature technology and are preferably characterized by:
  their viscosity: they are preferably mainly creams,
  their appearance, that can range from opaque to translucent,
  their pH, that ranges from 3 to 8,
  the small size of the droplets of the oily phase,
  their stability: the variation in viscosity after two months at 45° C. is less than or equal to 33% relative to the time 24 h at ambient temperature (20-25° C.).

Thus, the emulsions according to the invention, despite the large amount of oils that they contain, are stable. The term "stable composition" is intended to mean a composition that remains macroscopically homogeneous after 2 months at 45° C. and for which the variation in viscosity (plus or minus) relative to the initial viscosity is less than or equal to 33% (measurement on a Rheomat 180). Such a stability means that no macroscopic phase separation nor any change in texture, such as the appearance of grains, occurs after this period of time.

The compositions according to the invention are preferably in the form of more or less thick creams that are opaque to translucent, and they may or may not be able to flow under their own weight according to their viscosity. For a cream, the viscosity measured at 25° C. with the Rheomat 180 measuring device at 200 rpm (revolutions per minute) should be greater than or equal to 1 Pa·s. The Rheomat 180 is equipped with a different rotor according to the viscosities, for example with a rotor 3 for the range of viscosities from 0.2 to 4 Pa·s, and with a rotor 4 for the range of viscosities greater than 2 Pa·s. When measured under the conditions indicated above, the viscosity of the compositions of the invention can range, for example, from 1 to 30 Pa·s, and preferably from 1 to 20 Pa·s. This viscosity is generally measured 10 minutes after the rotation of the rotor has begun.

The mean size of the droplets of oily phase is measured by light diffraction using a Mastersizer 2000 particle sizer (sold by Malvern Instruments). These measurements are carried out on the emulsion diluted in a solution of SDS (sodium dodecyl sulphate) at 1% in water. A computer program makes it possible to obtain the mean diameter by volume D[4.3] (μm) (see operators guide, Malvern Instruments, December 1998, p. 61 to 67).

The mean size D[4.3] (μm) of the droplets of oily phase of the composition of the invention ranges from 0.09 μm to 4 μm, more particularly from 0.1 μm to 2 μm, and preferably from 0.1 μm to 1 μm.

Emulsifying System

The emulsifying system (B) used in the composition according to the invention comprises one or more emulsifiers whose solubility in the oil increases with the increase in temperature, which emulsifiers make it possible to obtain emulsions by phase temperature inversion. The HLB (hydrophilic lipophilic balance) of these emulsifiers ranges from 8 to 18, and preferably from 10 to 16, and these emulsifiers are chosen from ethoxylated fatty alcohols, ethoxylated fatty acids, partial glycerides of ethoxylated fatty acids, polyglycerolated fatty acid triglycerides and ethoxylated derivatives thereof, and mixtures thereof.

The emulsifiers are preferably chosen from ethoxylated fatty alcohols or ethoxylated fatty acids having the formulae (I) and (II) below:

$$R-O-(CH_2-CH_2-O)_mH \qquad (I)$$

$$R-COO-(CH_2-CH_2-O)_mH \qquad (II)$$

where R is a saturated or unsaturated, linear or branched hydrocarbon-based chain having from 10 to 24 carbon atoms, and m is an integer ranging from 8 to 50.

As ethoxylated fatty alcohols, mention may, for example, be made of the addition products of ethylene oxide with lauryl alcohol, in particular those containing from 9 to 50 oxyethylenated groups (having CTFA names Laureth-9 to Laureth-50); the addition products of ethylene oxide with behenyl alcohol, in particular those containing from 9 to 50 oxyethylenated groups (having CTFA names Beheneth-9 to Beheneth-50); the addition products of ethylene oxide with cetearyl alcohol (mixture of cetyl alcohol and of stearyl alcohol) in particular those containing from 9 to 30 oxyethylenated groups (having CTFA names Ceteareth-9 to Ceteareth-30); the addition products of ethylene oxide with cetyl alcohol, in particular those containing from 9 to 30 oxyethylenated groups (having CTFA names Ceteth-9 to Ceteth-30); the addition products of ethylene oxide with stearyl alcohol, in particular those containing from 9 to 30 oxyethylenated groups (having CTFA names Steareth-9 to Steareth-30; the addition products of ethylene oxide with isostearyl alcohol, in particular those containing from 9 to 50 oxyethylenated groups (having CTFA names Isosteareth-9 to Isosteareth-50); and mixtures thereof.

As ethoxylated fatty acids, mention may, for example, be made of the addition products of ethylene oxide with lauric acid, palmitic acid, stearic acid or behenic acid, and mixtures thereof, in particular those containing from 9 to.50 oxyethylenated groups, such as laurates of PEG-9 to PEG-50 (having CTFA names: PEG-9 laurate to PEG-50 laurate); palmitates of PEG-9 to PEG-50 (having CTFA names: PEG-9 palmitate to PEG-50 palmitate); stearates of PEG-9 to PEG-50 (having CTFA names: PEG-9 stearate to PEG-50 stearate); palmitostearates of PEG-9 to PEG-50; behenates of PEG-9 to PEG-50 (having CTFA names: PEG-9 behenate to PEG-50 behenate); and mixtures thereof.

Mixtures of these oxyethylenated derivatives of fatty alcohols and of fatty acids can also be used.

Preferably, the emulsifying system of the composition of the invention contains, as emulsifier, at least one ethoxylated fatty alcohol, and more particularly beheneth-10.

The emulsifying system may also contain one or more co-emulsifiers. As co-emulsifiers, mention may, for example, be made of fatty alcohols having 8 to 30 carbon atoms, for instance cetyl alcohol, stearyl alcohol or behenyl alcohol; fatty acids having 8 to 30 carbon atoms, for instance palmitic acid, stearic acid or behenic acid; fatty esters of glycerol, for instance glyceryl stearate; oxyethylenated derivatives of these fatty alcohols, fatty acids and fatty esters of glycerol, containing 2 to 8 ethylene oxide groups, and mixtures thereof.

The emulsifying system is present in an amount ranging from 2 to 20%, more preferably from 3 to 16%, and better still from 3 to 11%, by weight relative to the total weight of the composition.

The emulsifying system (B)/lipophilic phase (A) weight ratio ranges from 0.04 to 0.2, preferably from 0.06 to 0.18. As indicated above, the term "lipophilic phase" is intended to mean all the constituents that are not hydrophilic and that are different from the emulsifiers or co-emulsifiers of the emulsifying system.

Lipophilic Phase

The lipophilic phase, also called oily or fatty phase, comprises the lipophilic constituents, i.e. oils and other lipophilic substances present in the composition, and also any lipophilic additives optionally present. The lipophilic phase contains at least one oil, in particular a cosmetic oil.

The lipophilic phase is present in an amount of at least 50% by weight relative to the total weight of the composition. The amount of lipophilic phase can range, for example, from 50 to 90% by weight, preferably from 60 to 80% by weight, relative to the total weight of the composition. The lipophilic phase may comprise only oils (liquid fatty substances) or it may comprise a mixture of oils and of other fatty substances. However, the amount of oils is preferably at least 40% by weight relative to the total weight. of the composition, and preferably at least 50% relative to the total weight of the composition.

Characteristically, the amount of synthetic or mineral hydrocarbon-based oils having a molecular weight greater than or equal to 360 g/mol is at least 25% of the total weight of the lipophilic phase, and preferably at least 30% of the total weight of the lipophilic phase. This amount preferably ranges from 25 to 100%, and better still from 30 to 100%, of the total weight of the lipophilic phase.

The term "oil" is intended to mean a fatty substance that is liquid at ambient temperature (25° C.).

The term "hydrocarbon-based oil" is intended to mean an oil containing mainly carbon atoms and hydrogen, and optionally ester, ether and/or fluorinated groups.

As mineral or synthetic hydrocarbon-based oils having a molecular weight greater than or equal to 360 g/mol, that can be used in the composition of the invention, mention may in particular be made of fatty acid esters, preferably those obtained from an alcohol comprising a saturated or unsaturated, linear or branched chain having from 1 to 30 carbon atoms and from a fatty acid comprising a linear or branched chain having from 3 to 30 carbon atoms, the total sum of carbon atoms of said esters being greater than or equal to 24; alkanes; and mixtures thereof.

As fatty acid esters, mention may, for example, be made of 2-ethylhexyl palmitate (or octyl palmitate), cetyl 2-ethylhexanoate, 2-octyldodecyl myristate, isocetyl stearate, isostearyl isostearate, 2-ethylhexyl stearate (or octyl stearate), octyldodecyl neopentanoate, cetearyl isononanoate, isodecyl isononanoate, pentaerythritol tetraisostearate, isotridecyl isononanoate, $C_{12}$-$C_{15}$ fatty alcohol benzoates (Finsolv TN from Finetex), and mixtures thereof.

As alkanes, mention may, for example, be made of petroleum jelly, liquid petroleum jelly, hydrogenated isoparaffins such as Parleam® oil sold by the company NOF Corporation (INCI name: Hydrogenated Polyisobutene), and mixtures thereof.

According to a more preferred embodiment of the invention, the composition according to the invention contains one or more fatty acid esters chosen from 2-ethylhexyl palmitate (or octyl palmitate) and cetyl 2-ethylhexanoate (or cetyl octanoate).

The composition may also contain up to 75% by weight, relative to the weight of the-oily constituents of the oily phase, of one or more other oils chosen from fatty acid esters having a molecular weight of less than 360 g/mol, ethers, plant oils, silicone oils, and fluoro oils, that may or may not be volatile. Mention may in particular be made, as oils of this type, of esters of molecular weight less than 360 g/mol, such as 2-ethylhexyl caprate/caprylate (or octyl caprate/caprylate), ethyl laurate, butyl laurate, hexyl laurate, isohexyl laurate, isopropyl laurate, methyl myristate, ethyl myristate, butyl myristate, isobutyl myristate, isopropyl myristate, 2-ethylhexyl monococoate (or octyl monococoate), methyl palmitate, ethyl palmitate, isopropyl palmitate, isobutyl palmitate, butyl stearate, isopropyl stearate, isobutyl stearate, isopropyl isostearate, 2-ethylhexyl pelargonate (or octyl pelargonate) 2-ethylhexyl hydroxystearate (or octyl hydroxystearate), decyl oleate, diisopropyl adipate, 2-diethylhexyl adipate (or dioctyl adipate), diisocetyl adipate, 2-ethylhexyl succinate (or octyl succinate), diisopropyl sebacate, 2-ethylhexyl malate (or octyl malate), pentaerythritol caprate/caprylate,2-ethylhexyl hexanoate, (or octyl hexanoate), octyldodecyl octanoate, isodecyl neopentanoate, isostearyl neopentanoate, isononyl isononanoate, isotridecyl isononanoate, lauryl lactate, myristyl lactate, cetyl lactate, myristyl propionate, 2-ethylhexyl 2-ethylhexanoate (or octyl 2-ethylhexanoate), 2-ethylhexyl octanoate (or octyl octanoate), and mixtures thereof; isopropyl lauroyl sarcosinate (Eldew SL 205 from Unipex), dicaprylyl carbonate (Cetiol CC from Cognis);
  ethers such as dicaprylyl ether (Cetiol OE from Cognis);
  hydrocarbon-based oils of plant origin, such as sweet almond oil, avocado oil, castor oil, coriander oil, olive oil, jojoba oil, sesame oil, groundnut oil, grapeseed oil, rape seed oil, coconut oil, hazelnut oil, shea butter, palm oil, apricot kernel oil, beauty-leaf oil, rice bran oil, corn germ oil, wheat germ oil, soybean oil, sunflower oil, evening primrose oil, safflower oil, passion flower oil, rye oil, caprylic/capric acid triglycerides such as those sold by the company Stearineries Dubois or those sold under the names Miglyol 810, 812 and 818 by the company Dynamit Nobel;
  volatile or non-volatile silicone oils, such as volatile or non-volatile polydimethylsiloxanes (PDMS) containing a linear or cyclic silicone chain, that are liquid or pasty at ambient temperature, in particular cyclopolydimethylsiloxanes (cyclomethicones) such as cyclohexasiloxane; polydimethylsiloxanes containing alkyl, alkoxy or phenyl groups that are pendent or at the end of the silicone chain, which groups have from 2 to 24 carbon atoms; phenyl silicones such as phenyl trimethicones, phenyl dimethicones, phenyltrimethyl-siloxydiphenylsiloxanes, diphenyl dimethicones, diphenylmethyldiphenyltrisiloxanes, 2-phenylethyltrimethyl siloxysilicates, polymethylphenylsiloxanes;

fluoro oils such as those that are partially hydrocarbon-based and/or silicone based, for instance those described in document JP-A-2-295912;

linear or branched hydrocarbon-based oils of mineral, synthetic or animal origin, chosen from isohexadecane, isododecane, $C_{8-9}$ and $C_{11-13}$ isoparaffins (CTFA name: $C_{89}$ Isoparaffin and $C_{11-13}$ Isoparaffin); and mixtures thereof.

The other lipophilic constituents that may be present in the lipophilic phase include, for example, waxes; gums such as silicone gums (dimethiconol); silicone resins such as trifluoromethyl($C_1$-$C_4$)alkyl dimethicone and trifluoropropyl dimethicone; pastes such as petrolatum; and mixtures thereof.

Aqueous Phase

The composition according to the invention comprises an amount of aqueous phase less than or equal to 45%, and preferably less than or equal to 30%, of the total weight of the composition, it being possible for this amount to range, for example, from 10 to 45% by weight, and preferably from 10 to 30% by weight, relative to the total weight of the composition. The amount of water in the aqueous phase can range, for example, from 50 to 100% by weight relative to the weight of the aqueous phase.

According to a preferred embodiment, the composition of the invention contains at least one polyol (or polyhydric alcohols) that is generally present in the aqueous phase. As polyols, mention-may, for example, be made of glycerol; glycols such as propylene glycol, butylene glycol, isoprene glycol and polyethylene glycols such as PEG-8; sorbitol; sugars such as glucose, fructose, maltose, lactose or sucrose; and mixtures thereof. The amount of polyols generally ranges from 0.1 to 60% by weight, and better still from 0.5 to 50% by weight, relative to the total weight of the aqueous phase.

The aqueous phase can contain, for example, besides the water and the polyol(s), one or more water-soluble solvents chosen from water-soluble lower alcohol(s). The term "lower alcohol" is intended to mean an alcohol containing from 1 to 8 carbon atoms. As lower alcohols, mention may, for example, be made of ethanol, isopropanol, butanol and mixtures thereof. When they are present in the composition of the invention, the water-soluble lower alcohol(s) may be in an amount ranging from 0.01 to 40% by weight, and preferably from 0.01 to 20% by weight, relative to the total weight of the aqueous phase.

Additives

The composition according to the invention may also contain any adjuvant or additive, for example those conventionally used in the fields under consideration, and in particular in the cosmetics or dermatological fields. Of course, those skilled in the art will take care to choose the optional additive(s) of the composition according to the invention in such a way that the advantageous properties intrinsically associated with the composition in accordance with the invention are not, or are not substantially, altered by the envisaged addition.

Among the conventional adjuvants that may be contained in the aqueous phase and/or in the oily phase of the emulsions in accordance with the invention (according to the water-soluble or liposoluble nature of these adjuvants), mention may in particular be made of foaming surfactants that are anionic (such as sodium lauryl ether sulphate, sodium alkyl phosphate or sodium trideceth sulphate), amphoteric (such as alkyl betaine or disodium cocoamphodiacetate) or non-ionic with an HLB greater than 10 (such as POE/PPG/POE, alkylpolyglucoside, or polyglyceryl-3 hydroxylauryl ether); preserving agents; sequestering agents (EDTA); antioxidants; fragrances; dyestuffs such as soluble dyes, pigments and pearlescent agents; matifying, tensioning, bleaching or exfoliating fillers; sunscreens; cosmetic or dermatological active agents and agents having the effect of improving the cosmetic properties of the skin, that are hydrophilic or lipophilic; electrolytes; hydrophilic or lipophilic, anionic, non-ionic, cationic or amphoteric, thickening or dispersing polymers. The amounts of these various adjuvants are those conventionally used in the field under consideration and are, for example, from 0.01 to 20% of the total weight of the composition.

As active agents that can be used in the composition of the invention, mention may, for example, be made of water-soluble or liposoluble vitamins such as vitamin A (retinol), vitamin E (tocopherol), vitamin C (ascorbic acid), vitamin B5 (panthenol) vitamin B3 (niacinamide), derivatives of these vitamins (in particular esters) and mixtures thereof; antiseptics; antibacterial active agents such as 2,4,4'-trichloro-2'-hydroxy diphenyl ether (or triclosan) or 3,4,4'-trichlorocarbanilide (or triclocarban); antisebohrreic agents; antimicrobial agents such as benzyl peroxide, salicylic acid, triclosan, azelaic acid or niacin (vit. PP); slimming agents such as caffeine; optical brighteners, and any active agent that is suitable for the final purpose of the composition, and mixtures thereof.

The amount of active agents depends on the desired aim. The active agent(s) may, for example, be present at a concentration ranging from 0.001 to 20%, preferably from 0.01 to 10% by weight, and better still from 0.05 to 5%, of the total weight of the composition.

The emulsions according to the invention can be obtained by a phase inversion process. This preparation process comprises:

1) Weighing out, into a container, all the constituents of the composition (with the exception of the thermosensitive starting materials, if there are any).
2) Homogenizing the mixture, for example by means of a Rayneri 350 rpm, and heating by gradually increasing the temperature, for example by means of a water bath, to a temperature greater than or equal to the phase inversion temperature T2, i.e. until a transparent or translucent phase (microemulsion or lamellar phase region) is obtained, followed by a more viscous white phase that indicates that the inverse emulsion (W/O) has been obtained.
3) Stopping the heating and maintaining the stirring until ambient temperature is again reached, passing through the phase inversion temperature T1, i.e. the temperature at which a fine O/W emulsion forms.
4) When the temperature has again dropped below the phase inversion temperature (T1) region, optionally adding the thermosensitive starting materials.

A stable O/W emulsion is obtained in which the droplets of oil are fine.

While not bound by theory, it is believed that in the microemulsion formation region (translucent mixture), the hydrophilic and hydrophobic interactions are equilibrated since the tendency of the surfactant is to form both direct micelles and inverse micelles. By heating beyond this region, formation of a W/O emulsion (white opaque mixture) is obtained since the surfactant promotes the formation of a water-in-oil emulsion. Then, during the cooling below the phase inversion region, the emulsion becomes an O/W emulsion.

Phase inversion emulsification is explained in detail in the work T. Förster, W von Rybinski, A. Wadle, Influence of microemulsion phases on the preparation of fine disperse emulsions, Advances in Colloid and interface sciences, 58, 119-149, 1995, mentioned here by way of reference.

The compositions according to the invention are preferably in the form of more of less supple creams, and they can in particular constitute cosmetic or dermatological compositions, for example cosmetic compositions for the treatment of keratin materials such as the skin, the mucous membranes, the eyelashes, the hair and the nails. They can also constitute, for example, makeup-removing compositions and/or cleansing compositions and/or care compositions for the skin, the mucous membranes such as the lips, and/or for the eyelashes, compositions for massaging facial skin or body skin, scrubbing (or exfoliating) compositions both for the face and for the hands (when the composition contains exfoliating particles), antisun compositions (UV protection) and aftersun compositions. They may also constitute makeup compositions for keratin materials and in particular the skin, the lips and the eyelashes, and more particularly such as foundations, lipsticks or lip glosses after the addition of suitable pigments and/or fillers.

The compositions according to the invention can also be used as shower care balms (to be rinsed, for example by massaging in the product until the oil is released, and then rinsing the skin which is then soft and moisturized); as conditioners and hair care balms; as shaving products; as masks, including an aftersun repairing mask; as a slimming poultice on a region of "orange peel skin" (to be massaged in and then rinsed off); as a massage balm; as a lip repairing balm to be rinsed off; as a balm for dry feet. In these uses, the product is subsequently rinsed off.

When the composition is an exfoliating product (also called cleansing product), the use comprises applying the product to the face or the hands or the body, in rubbing for one or two minutes, and then in rinsing. The skin is then smooth, soft and cleansed.

A subject of the invention is also the cosmetic use of the composition as defined above, as a skincare product, as a hygiene product, as a hair care product, as an antisun product and as a makeup product.

Another subject of the invention is a process for the cosmetic treatment of a keratin material, such as the skin, the scalp, the hair, the eyelashes, the eyebrows, the nails or the mucous membranes, wherein a composition as defined above is applied to the keratin material.

The keratin material is preferably the skin.

The compositions according to the invention can be used differently according to the desired applications, for example:
  applied only (without rinsing), as a care product for the face or the body, or a makeup product for the skin, the lips or the eyes, or as an antisun product, for example,
  wiped, rinsed with water or with a tonic, as a makeup-removing product,
  rinsed with water, as a hair care product after shampooing.

The examples indicated below will make it possible to understand the invention more clearly without, however, being limiting in nature. The amounts indicated are as % by weight unless otherwise indicated. The names are chemical names and CTFA names according to the compounds. In certain examples, the temperatures T1 and T2 corresponding to the temperatures bordering the phase inversion region are indicated.

The examples realized were subjected to viscosity measurements for demonstrating their stability over time.

The starting materials used in the examples are as follows:
(1) Eumulgin BA 10® sold by Cognis=oxyethylenated behenyl alcohol (10 OE),
(2) Isopropyl Palmitate® sold by Cognis=isopropyl palmitate,
(3) Isocetyl Stearate® sold by Stearineries Dubois=isocetyl stearate,
(4) Cetiol OE® sold by Cognis=dicaprylyl ether
(5) Cegesoft C 24® sold by Cognis or Ceraphyl 368® sold by ISP=2-ethylhexyl palmitate.

| Composition | Example 1 | Example 2 |
|---|---|---|
| Eumulgin BA 10 ® (1) | 5 | 5 |
| Isocetyl Stearate ® (3) (MW 509 g/mol) | 11.55 | 16.17 |
| Cetiol OE ® (4) (MW 240 g/mol) | 23.45 | 46.9 |
| Cegesoft C 24 ® (5) (MW 368 g/mol) | 35 | 0 |
| Propyl paraben | 0.15 | 0.15 |
| Methyl paraben | 0.15 | 0.15 |
| Chlorhexidine digluconate | 0.25 | 0.25 |
| Glycerol | 10 | 10 |
| Deionized water | 14.45 | 14.45 |
| Total | 100 | 100 |
| % total of surfactants (SA) | 5 | 5 |
| % total of oily constituents | 70 | 63.07 |
| SA/oily constituent ratio | 0.07 | 0.07 |
| % oil of MW ≥ 360 g/mol relative to the total oily constituents | 66.5 | 25.6 |
| T1 (° C.) | 75 | 72 |
| T2 (° C.) | 81 | 78 |
| Appearance | Very smooth, shiny, white opaque emulsion | Very smooth, shiny, white opaque emulsion |
| pH | 5.7 | 6 |
| Macroscopic appearance after 2 months at 45° C. | Homogeneous | Homogeneous |
| Viscosity (Pa · s) at 24 h at ambient temperature, at t10 minutes | 6.9 | 5.4 |
| Viscosity (Pa · s) after 2 months at 45° C. at t10 minutes | 4.7 | 4 |
| Variation in viscosity relative to 24 h at ambient temperature | −32% | −26% |
| Conclusion | Acceptable viscosity variation | Acceptable viscosity variation |

| Composition | Example 3 | Example 4 |
|---|---|---|
| Eumulgin BA 10 ® (1) | 5 | 5 |
| Isocetyl Stearate ® (3) (MW 509 g/mol) | 0 | 70 |
| Cegesoft C 24 ® (5) (MW 368 g/mol) | 70 | 0 |
| Propyl paraben | 0.15 | 0.15 |
| Methyl paraben | 0.15 | 0.15 |
| Chlorhexidine digluconate | 0.25 | 0.25 |
| Glycerol | 10 | 10 |
| Deionized water | 14.45 | 14.45 |
| Total | 100 | 100 |
| % total of surfactants (SA) | 5 | 5 |
| % total of oily constituents | 70 | 70 |
| SA/oily constituent ratio | 0.07 | 0.07 |
| % oil of MW ≥ 360 g/mol relative to the total oily constituents | 100 | 100 |

| | | |
|---|---|---|
| T1 (° C.) | 73 | 77 |
| T2 (° C.) | 85 | 85 |
| Appearance | Smooth, homogeneous, opaque/translucent emulsion | White emulsion |
| pH | 5.7 | 6 |
| Macroscopic appearance after 2 months at 45° C. | Homogeneous | Homogeneous |
| Viscosity (Pa · s) at 24 h at ambient temperature, at t10 minutes | 6.9 | 7.3 |
| Viscosity (Pa · s) after 2 months at 45° C. at t10 minutes | 6.6 | 7.8 |
| Variation in viscosity relative to 24 h at ambient temperature | −4% | +6% |
| Conclusion | Very small variation in viscosity | Very small variation in viscosity |

| Composition | Example 5 |
|---|---|
| Eumulgin BA 10 ® (1) | 5 |
| Cegesoft C 24 ® (5) (MW 368 g/mol) | 64 |
| Propyl paraben | 0.15 |
| Methyl paraben | 0.15 |
| Chlorhexidine digluconate | 0.25 |
| Glycerol | 10 |
| Deionized water | 18.45 |
| Ethanol | 2 |
| Total | 100 |
| % total of surfactants (SA) | 5 |
| % total of oily constituents | 64 |
| SA/oily constituents ratio | 0.078 |
| % oil of MW ≥ 360 g/mol relative to the total oily constituents | 100 |
| T1 (° C.) | 73 |
| T2 (° C.) | 85 |
| Appearance | Very smooth, shiny, white opaque emulsion |
| pH | 6.7 |
| Macroscopic appearance after 2 months at 45° C. | Homogeneous |
| Viscosity (Pa · s) at 24 h at ambient temperature, at t10 minutes | 5.9 |
| Viscosity (Pa · s) after 2 months at 45° C. at t10 minutes | 7.1 |
| Variation in viscosity relative to 24 h at ambient temperature | 20% |
| Conclusion | Acceptable viscosity variation |

III. COMPARATIVE EXAMPLES

| Composition | Comparative Example 1 | Comparative Example 2 |
|---|---|---|
| Eumulgin BA 10 ® (1) | 5 | 5 |
| Isopropyl Palmitate ® (2) (MW 298 g/mol) | 0 | 70 |
| Cetiol OE ® (4) (MW 240 g/mol) | 70 | 0 |
| Propyl paraben | 0.15 | 0.15 |
| Methyl paraben | 0.15 | 0.15 |
| Chlorhexidine digluconate | 0.25 | 0.25 |
| Glycerol | 10 | 10 |
| Deionized water | 14.45 | 14.45 |
| Total | 100 | 100 |
| % total of surfactants (SA) | 5 | 5 |
| % total of oily constituents | 70 | 70 |
| SA/oily constituents ratio | 0.07 | 0.07 |
| % oil of MW ≥ 360 g/mol relative to the total oily constituents | 0 | 0 |
| T1 (° C.) | None | None |
| T2 (° C.) | Greater than 95° C. | Greater than 95° C. |
| Appearance | There is no emulsion: two phases | There is no emulsion: two phases |
| Conclusion | Impossible to produce the emulsion: the MW of the oil (240 g/mol) is too low | Impossible to produce the emulsion: the MW of the oil (298 g/mol) is too low |

These comparative examples show that, in the absence of oil having an MW>360 g/mol, emulsions cannot be obtained.

| Composition | Comparative Example 3 | Comparative Example 4 |
|---|---|---|
| Eumulgin BA 10 ® (1) | 5 | 5 |
| Isopropyl Palmitate ® (2) (MW 298 g/mol) | 35 | 20 |
| Isocetyl Stearate ® (3) (MW 509 g/mol) | 11.55 | 16.5 |
| Cetiol OE ® (4) (MW 240 g/mol) | 23.45 | 33.50 |
| Propyl paraben | 0.15 | 0.15 |
| Methyl paraben | 0.15 | 0.15 |
| Chlorhexidine digluconate | 0.25 | 0.25 |
| Glycerol | 10 | 10 |
| Deionized water | 14.45 | 14.45 |
| Total | 100 | 100 |
| % total of surfactants (SA) | 5 | 5 |
| % total of oily constituents | 70 | 70 |
| SA/oily constituents ratio | 0.07 | 0.07 |
| % oil of MW ≥ 360 g/mol relative to the total oily constituents | 16.5% | 23.6% |
| T1 (° C.) | 68 | 70 |
| T2 (° C.) | 75 | 75 |
| Appearance | Smooth, translucent/opaque emulsion | Very smooth, translucent/opaque emulsion |
| pH | 6 | 5.7 |
| Macroscopic appearance after 2 months at 45° C. | Slightly granular | Slightly granular |
| Viscosity (Pa · s) at 24 h at ambient temperature, at t10 minutes | 5.7 | 5.9 |
| Viscosity (Pa · s) after 2 months at 45° C. at t10 minutes | 3.1 | 3.8 |
| Variation in viscosity relative to 24 h at ambient temperature | −46% | −35% |
| Conclusion | Variation in viscosity too great | Variation in viscosity too great |

These comparative examples show that, in the absence of a sufficient amount of oil having an MW>360 g/mol, the emulsions obtained have a viscosity that varies too much over time for it to be possible for the emulsions to be considered as stable emulsions.

The above written description of the invention provides a manner and process of making and using it such that any person skilled in this art is enabled to make and use the same, this enablement being provided in particular for the subject matter of the appended claims, which make up a part of the original description and including a composition for topical application in the form of an oil-in-water emulsion, wherein it contains:

a lipophilic phase (A) present in an amount of at least 50% by weight relative to the total weight of the composition, the lipophilic phase comprising at least 25% by weight of one or more synthetic or mineral hydrocarbon-based oils having a molecular weight greater than or equal to 360 g/mol, relative to the total weight of the lipophilic phase, an aqueous phase (C) present in an amount of less than or equal to 45% by weight relative to the total weight of the composition, an emulsifying system (B) present in an amount of 2 to 20% by weight relative to the total weight of the composition and comprising at least one emulsifier having an HLB ranging from 8 to 18, chosen from ethoxylated fatty alcohols, ethoxylated fatty acids, partial glycerides of ethoxylated fatty acids, polyglycerolated fatty acid triglycerides and ethoxylated derivatives thereof and mixtures thereof, the emulsifying system (B)/lipophilic phase (A) ratio ranging from 0.04 to 0.2.

Similarly fully described and enabled is a process for preparing a composition according to the invention comprising:

1) Weighing out, into a container, all the constituents of the composition (with the exception of the thermosensitive starting materials).
2) Homogenizing the mixture, and heating by gradually increasing the temperature, by means of a water bath, to a temperature greater than or equal to the phase inversion temperature T2.
3) Stopping the heating and maintaining the stirring until ambient temperature is again reached, passing through the phase inversion temperature T1.
4) When the temperature has again dropped below the phase inversion temperature (T1) region, optionally adding the thermosensitive starting materials.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out. Terms such as "contain(s)" and the like as used herein are open terms meaning 'including at least' unless otherwise specifically noted.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition in the form of an oil-in-water emulsion, comprising:
   a lipophilic phase (A) present in an amount of from 60% to 80% by weight relative to a total weight of the composition, the lipophilic phase comprising from 30% to 100% by weight of one or more synthetic or mineral hydrocarbon-based oils having a molecular weight greater than or equal to 360 g/mol relative to a total weight of the lipophilic phase;
   an emulsifying system (B) present in an amount of from 2 to 5% by weight relative to the total weight of the composition, wherein the composition has only a single emulsifier that is an ethoxylated fatty alcohol having an HLB ranging from 8 to 18 or only a mixture of ethoxylated fatty alcohols having an HLB ranging from 8 to 18;
   an aqueous phase (C) present in an amount of from 10% to 30% by weight relative to the total weight of the composition;
   wherein a weight ratio of the emulsifying system (B) to the lipophilic phase (A) is from 0.04 to 0.2.

2. The composition according to claim 1, obtained by phase inversion emulsification.

3. The composition according to claim 1, wherein a mean size of droplets the lipophilic phase (A) D[4.3] is 0.09 μm to 4 μm.

4. The composition according to claim 1, having a viscosity at 25° C. of greater than or equal to 1 Pa·s.

5. The composition according to claim 1, wherein the synthetic or mineral hydrocarbon-based oils having a molecular weight of greater than or equal to 360 g/mol comprise at least one member selected from the group consisting of fatty acid esters obtained from an alcohol comprising a saturated or unsaturated, linear or branched chain having from 1 to 24 carbon atoms and a fatty acid comprising a linear or branched chain having from 3 to 24 carbon atoms, the total sum of carbon atoms of said esters being greater than or equal to 24, and alkanes.

6. The composition according to claim 1, wherein the synthetic or mineral hydrocarbon-based oils having a molecular weight of greater than or equal to 360 g/mol are comprise at least one member selected from the group consisting of 2-ethylhexyl palmitate, cetyl 2-ethylhexanoate, 2-octyldodecyl myristate, isocetyl stearate, isostearyl isostearate, 2-ethylhexyl stearate, octyldodecyl neopentanoate, cetearyl isononanoate, isodecyl isononanoate, pentaerythritol tetraisostearate, isotridecyl isononanoate, C12-C15 fatty alcohol benzoates, petroleum jelly, liquid petroleum jelly and hydrogenated isoparaffin.

7. The composition according to claim 1, wherein the synthetic or mineral hydrocarbon-based oils having a molecular weight of greater than or equal to 360 g/mol are present in an amount of from 66.5% to 100% by weight relative to a total weight of oily constituents of the lipophilic phase (A).

8. The composition according to claim 1, comprising at least one polyol.

9. The composition according to claim 8, wherein the polyol comprises at least one member selected from the group consisting of glycerol, glycols and sugars.

10. The composition according to claim 8, wherein the polyol is present in an amount of from 5 to 20% by weight relative to the total weight of the composition.

11. The composition according to claim 1, wherein said composition is a cosmetic or dermatological composition.

12. The composition according to claim 1, wherein said composition is a makeup-removing composition and/or a cleansing composition for the skin, the lips and/or the eyelashes, a composition for massaging facial skin and/or body skin, an exfoliating composition, an antisun composition or an aftersun composition, a shower care balm, a conditioner composition, a hair care balm, a shaving product, a mask, a slimming poultice, a massage balm, a lip repairing balm, or a balm for dry feet.

13. A process, comprising applying the composition according to claim 1 a keratin material.

14. The process according to claim 11, wherein said composition is applied to skin, the lips and/or the eyelashes.

* * * * *